(12) United States Patent
Berra et al.

(10) Patent No.: US 7,279,003 B2
(45) Date of Patent: Oct. 9, 2007

(54) STENT GRAFT TAPERED SPRING (75) Inventors: Humberto Berra, Cooper City, FL (US); Michel Letort, Prevessins (FR)

(73) Assignee: Medtronic Vascular, Inc., Santa Rosa, CA (US)

( * ) Notice: Subject to any disclaimer, the term of this patent is extended or adjusted under 35 U.S.C. 154(b) by 858 days.

(21) Appl. No.: 10/423,163

(22) Filed: Apr. 24, 2003

(65) Prior Publication Data
US 2004/0215319 A1 Oct. 28, 2004

(51) Int. Cl.
A61F 2/06 (2006.01)
(52) U.S. Cl. ............... 623/1.13; 623/1.15
(58) Field of Classification Search ............. 623/1.11, 623/1.12, 1.13, 1.15, 1.16, 1.23, 1.35, 1.51; 606/191, 192, 194, 195, 198
See application file for complete search history.

(56) References Cited

U.S. PATENT DOCUMENTS

| 5,907,893 A | 6/1999 | Zadno-Azizi et al. ......... 29/6.1 |
| 6,164,339 A * | 12/2000 | Greenhalgh ................ 623/1.51 |
| 6,290,720 B1 | 9/2001 | Khosravi et al. ........... 623/1.13 |
| 6,322,585 B1 | 11/2001 | Khosravi et al. ........... 623/1.11 |
| 6,325,820 B1 | 12/2001 | Khosravi et al. ........... 623/1.13 |
| 6,327,772 B1 | 12/2001 | Zadno-Azizi et al. ......... 29/557 |
| 2001/0029396 A1 | 10/2001 | Bigus et al. .............. 623/1.11 |
| 2002/0052643 A1 | 5/2002 | Wholey et al. ............. 623/1.13 |
| 2002/0120327 A1 | 8/2002 | Freislinger et al. ......... 623/1.16 |
| 2002/0183833 A1 | 12/2002 | Springer et al. ............ 623/1.22 |
| 2004/0106978 A1* | 6/2004 | Greenberg et al. .......... 623/1.13 |

FOREIGN PATENT DOCUMENTS

| EP | 1177780 | 2/2002 |
| WO | 9727959 | 8/1997 |
| WO | 0028921 | 5/2000 |
| WO | 0044308 | 8/2000 |
| WO | 0061034 | 10/2000 |

OTHER PUBLICATIONS

Kawamura et al., "Emergent Endovascular Stent-Graft Placement to Treat Ruptured Stanford Type B Acute Aortic Dissection," Journal of Vascular Surgery, vol. 38, No. 5, pp. 668-671 Mar. 2004.

* cited by examiner

Primary Examiner—Kevin T. Truong
(74) Attorney, Agent, or Firm—Serge Hodgson (57) ABSTRACT A stent graft includes a stent graft material of cylindrical shape and tapered stent springs coupled to the stent graft material. Each stent spring includes a first stent cell and a second stent cell contiguous with the first stent cell. The first stent cell and the second stent cell are coupled. The second stent cell of each tapered stent spring is smaller than the first stent cell thereby defining a tapered shape to the tapered stent springs. The stent graft is placed in a curved segment of a tortuous body lumen and rotationally positioned such that the smallest stent cell of each tapered stent spring is placed at an inside radius of the curved segment.

16 Claims, 7 Drawing Sheets

STENT GRAFT TAPERED SPRING

BACKGROUND OF THE INVENTION

1. Field of the Invention

The present invention relates to endoluminal structures. More particularly, the present invention relates to endoluminal stent grafts for use in curved body lumens.

2. Description of the Related Art

A conventional stent graft typically includes a radially expandable stent, formed from a plurality of uniform annular stent springs, and a cylindrical shape graft material to which the stent springs are coupled. Stent grafts are well known for use in reinforcing or holding open the interior wall of a generally tubular shape human vascular and other body lumen.

At deployment, after percutaneous insertion and transluminal transport to the point of use within a damaged or diseased body lumen, e.g., an aneurysmal artery, the stent graft is radially expanded. A stent graft is self-expandable or expandable by application of pressure applied outwardly to the interior portion of the stent graft. After deployment, the stent graft should be somewhat rigid to provide sufficient support to the body lumen.

Figure 1A:
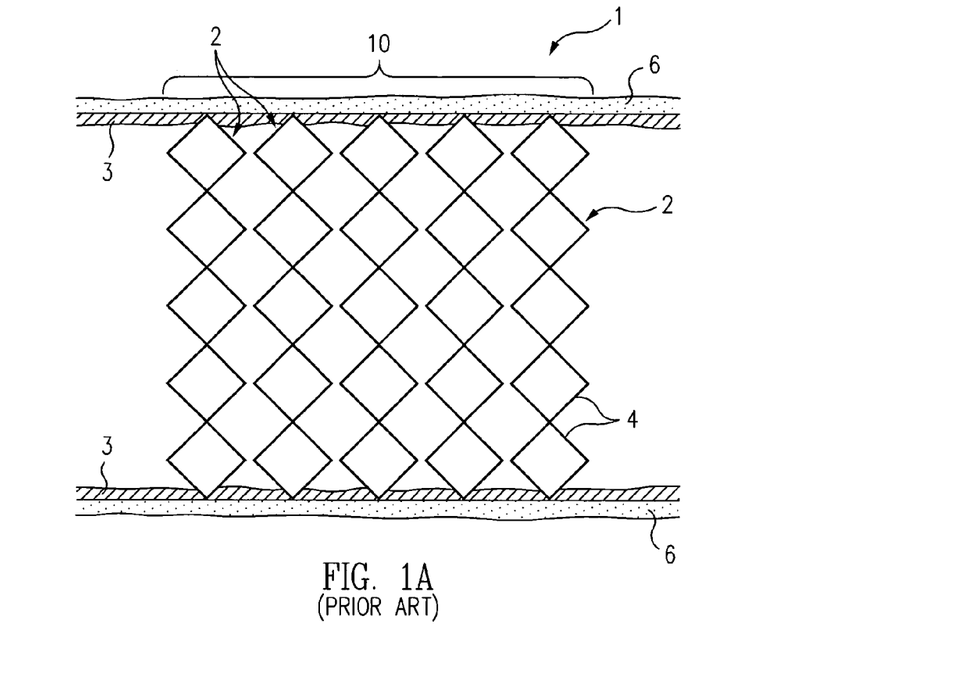
FIG. 1A is a plan view of a stent graft, according to the prior art, deployed within a substantially linear segment of a body lumen.

FIG. 1A is a plan view of stent graft 1, according to the prior art, deployed within a substantially linear segment 10 of a body lumen 6. Stent graft 1 includes a plurality of closely spaced uniform stent springs 2, each formed from a plurality of identical, coupled stent cells 4 into an annular shaped ring around a cylindrical shape stent graft material 3. Within linear segment 10 of body lumen 6, stent graft 1 experienced little or no axial bending force since linear segment 10 of body lumen 6 generally comported with the cylindrical shape of stent graft 1.

Figure 1B:
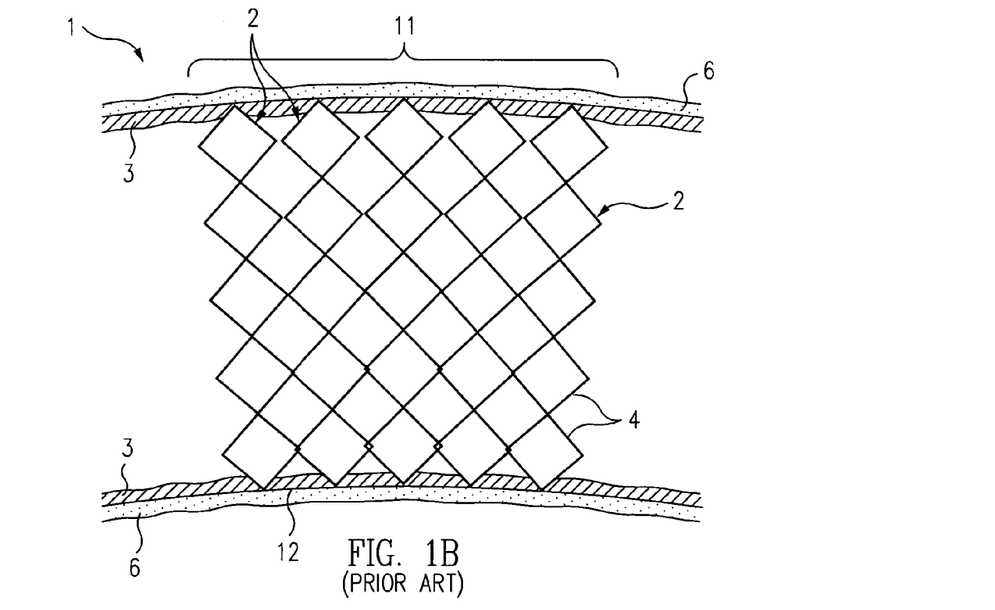
FIG. 1B is a plan view of a stent graft, according to the prior art, deployed within a curved segment of a body lumen.

However, human luminal systems are tortuous by nature. FIG. 1B is a plan view of stent graft 1, according to the prior art, deployed within a curved segment 11 of body lumen 6. As shown, curved segment 11 includes an interior radius 12.

Within curved segment 11, stent graft 1 is subject to a bending force imposed by curved segment 11 of body lumen 6. Thus, after deployment in a tortuous body lumen, conventional stent grafts were often subjected to significant axial bending and flexing.

It was necessary to limit the amount of axial bending allowed in a deployed stent graft to avoid stent cell overlap at inside radius 12 of curved segment 11 of body lumen 6. Stent cell overlap caused binding or kinking of the stent graft 1 resulting in restriction of flow through the body lumen. Accordingly, the use of conventional stent grafts was limited to certain applications that avoided damage to or destruction of the stent graft from excessive axial bending.

SUMMARY OF THE INVENTION

A stent graft includes a stent graft material of cylindrical shape and tapered stent springs coupled to the stent graft material. Each tapered stent spring includes a first stent cell and second stent cell contiguous with the first stent cell, wherein the second stent cell is coupled to the first stent cell, and further wherein the second stent cell is smaller than the first stent cell. In one embodiment, each stent cell is open and defines a serpentine shape. In another embodiment, each stent cell is closed and each stent cell defines a diamond shape.

When properly positioned rotationally within a tortuous body lumen such that the smallest stent cells are placed along the inside radius of a curved segment of the tortuous body lumen, the tapered stent springs provide axial flexibility to the stent graft in at least one direction. Thus, the stent graft easily conforms to the curved segment of the tortuous body lumen while maintaining support for the lumen at the curved segment.

Accordingly, use of the stent graft avoids restriction of flow through the body lumen resulting from binding or kinking of the stent graft at curved segments of the body lumen.

BRIEF DESCRIPTION OF THE DRAWINGS

Common reference numerals are used throughout the drawings and detailed description to indicate like elements.

DETAILED DESCRIPTION

Stent graft 100 (FIG. 2A) includes a plurality of spaced apart tapered stent springs 102 coupled to a cylindrical shape stent graft material 103. A tortuous body lumen, such as an artery system 106, in which stent graft 100 is deployed, includes a curved segment, e.g., a thoracoabdominal aortic arch 107, which is diseased or damaged and which requires endoluminal prosthetic support. Thus, stent graft 100 is percutaneously inserted into artery system 106, transported transluminally to aortic arch 107, and deployed to support aortic arch 107.

Figure 2A:
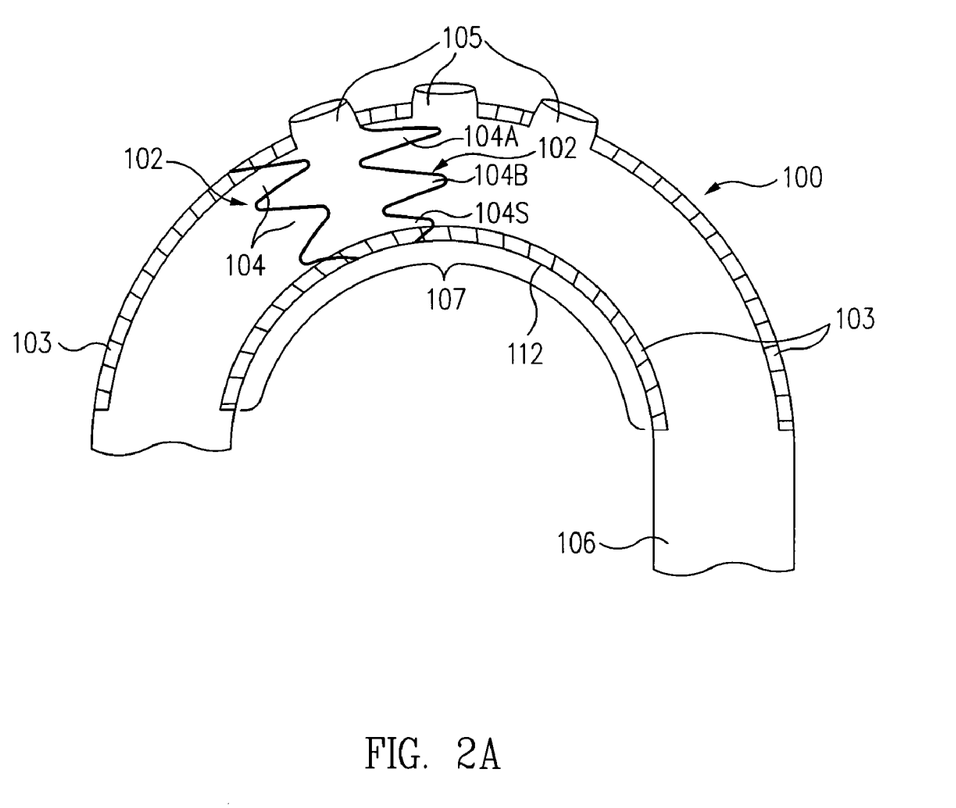
FIG. 2A is a plan view of a bent stent graft, deployed within an aortic arch, in one embodiment according to the present invention.

As shown, in one embodiment, stent graft material 103 may define one or more perimeter openings 105, (fenstrations), that allow fluid flow through perimeter openings 105, out of stent graft 100, into other segments (not shown) of artery system 106.

Tapered stent springs 102 provide axial flexibility to stent graft 100 in at least one direction. Accordingly, stent graft 100 easily conforms to the curved shape of aortic arch 107 of artery system 106 while maintaining support for aortic arch 107. Use of stent graft 100 avoids overlap of stent cells 104 at an inside radius 112 of aortic arch 107 and restriction of blood flow through artery system 106 resulting from binding or kinking of stent graft 100 at aortic arch 107.

As discussed more fully below, tapered stent springs 102 are integral and define a wave-like, serpentine shape. Tapered stent springs 102 include a plurality of open, i.e., with a broken incomplete perimeter, stent cells 104, including first stent cell 104A and second stent cell 104B contiguous with first stent cell 104A. The serpentine shape of tapered stent springs, according to alternate embodiments, may, for example, be zigzagged or stepped.

Contiguous stent cells, such as stent cells 104A and 104B, while similarly shaped, vary in size. In addition, as also discussed more fully below, tapered stent springs 102 include smallest stent cells 104S, in which stent cell size within a particular stent spring 102 is minimum.

Figure 2B:
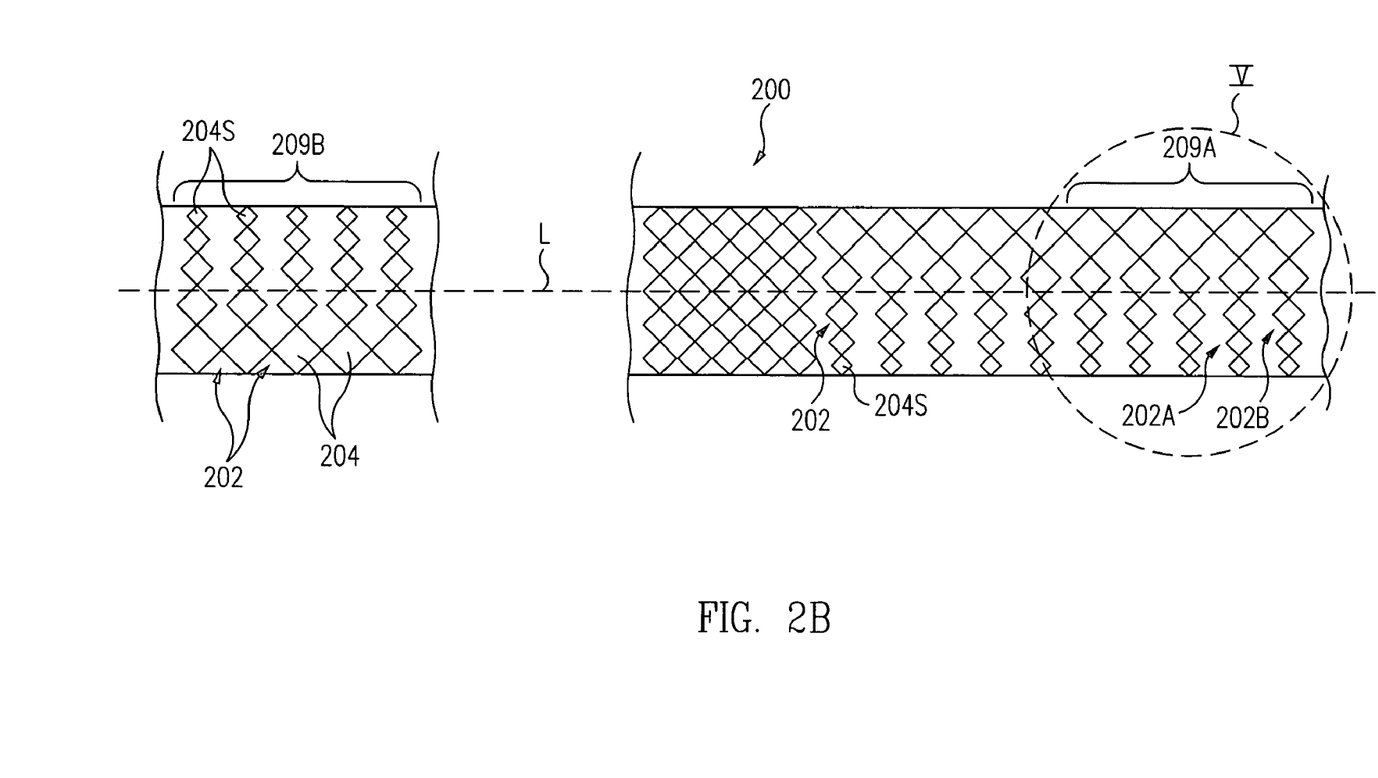
FIG. 2B is a plan view of a stent graft, before deployment, in one embodiment according to the present invention.
Figure 2C:
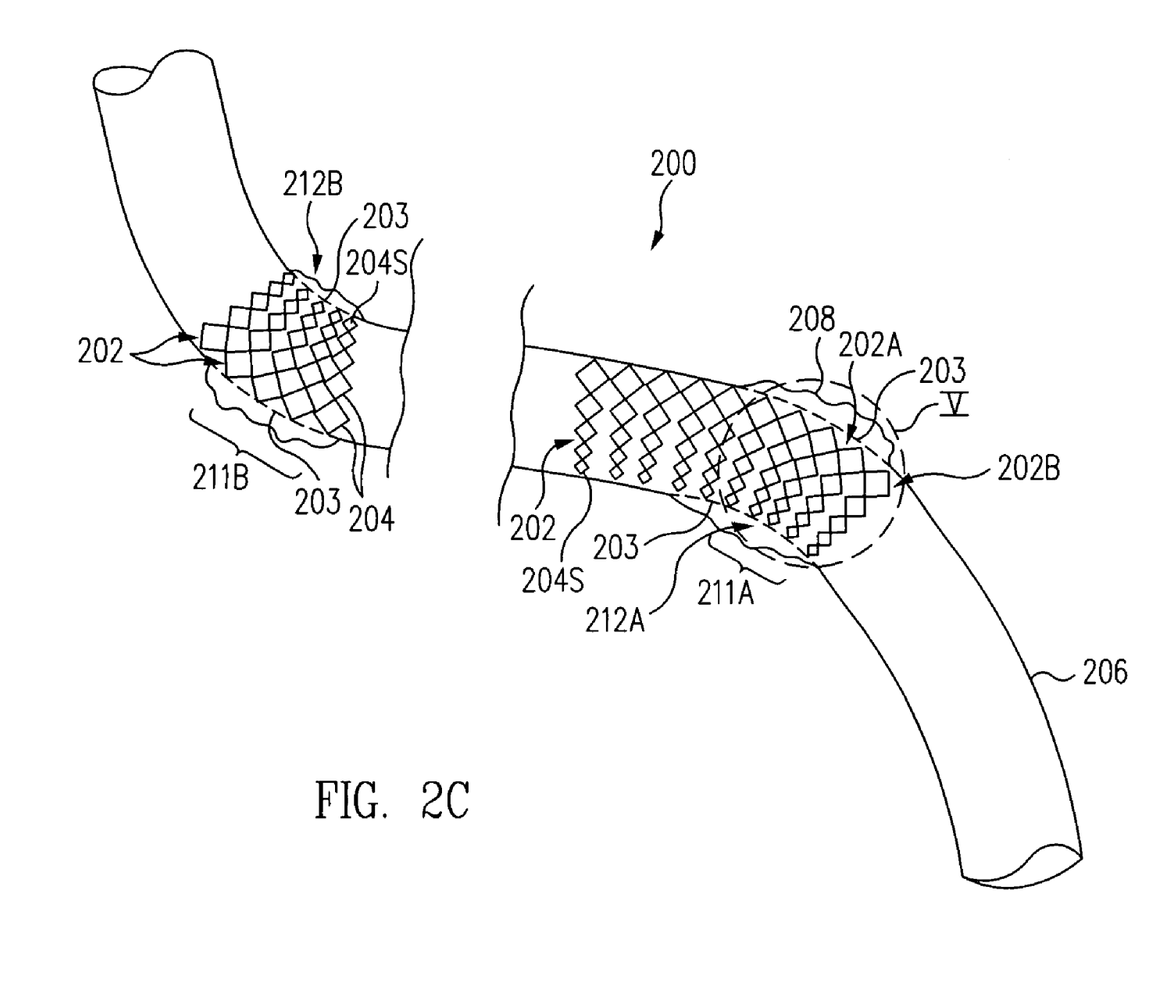
FIG. 2C is a partial cutaway plan view of an artery system containing a deployed stent graft in one embodiment according to the present invention.

Although stent cells of a particular shape are described above, in light of this disclosure, it is understood that tapered stent springs may include stent cells of other shapes. For example, in FIGS. 2B, 2C, and 3, tapered stent springs 202 include a plurality of diamond shape stent cells 204. More particularly, FIG. 2B is a plan view of stent graft 200, before deployment in artery system 206 (FIG. 2C). As shown, stent graft 200 includes a central axis L.

Adjacent tapered stent springs 202, such as first tapered stent spring 202A and second tapered stent spring 202B, of stent graft 200 are spaced apart and coupled, e.g., sewn, to cylindrical shape stent graft material 203 (FIG. 2C) with sutures (not shown). Tapered stent springs 202 form independent annular rings around cylindrical shape stent graft material 203.

In one embodiment, cylindrical shape stent graft material 203 is inside tapered stent springs 202. In another embodiment, stent graft material 203 is outside tapered stent springs 202.

Figure 3:
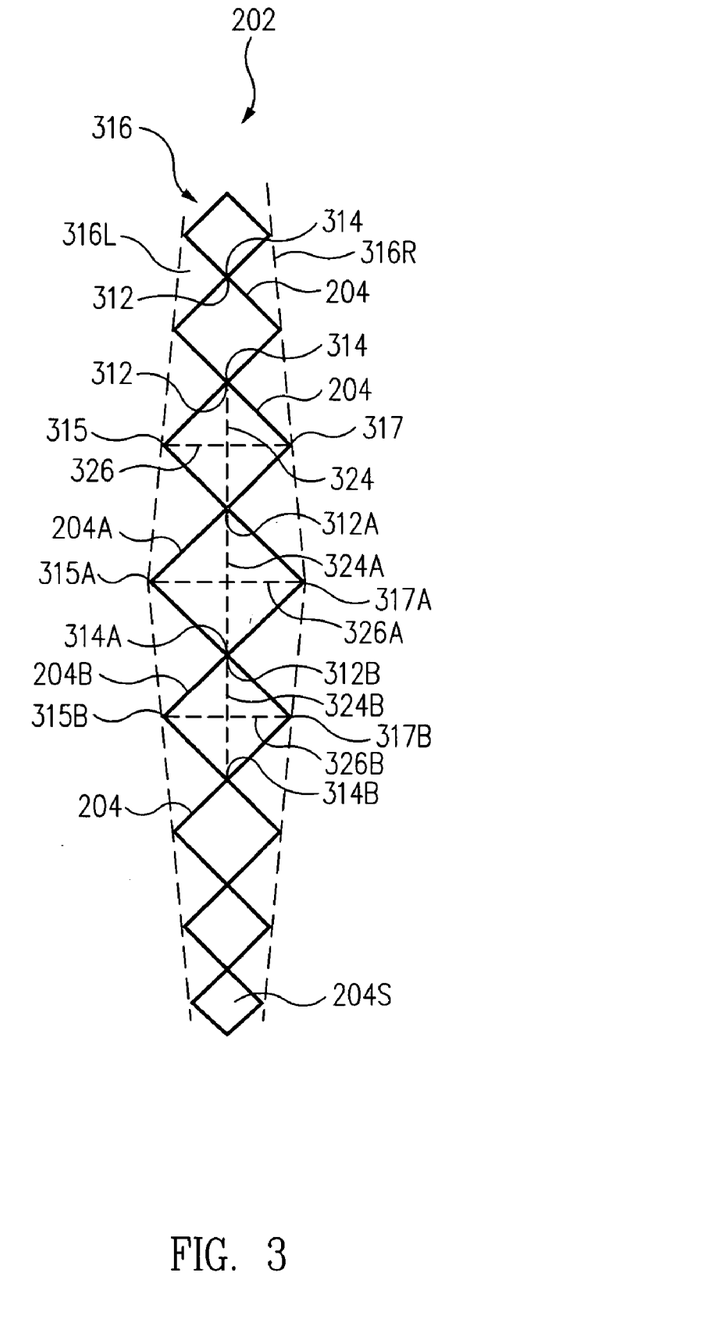
FIG. 3 is a flat layout view of an individual tapered stent spring of the stent graft of FIGS. 2B and 2C.

FIG. 3 is a view an individual tapered stent spring 202 of stent graft 200 of FIGS. 2B and 2C, opened up and shown in a flat layout view of one cylindrical element. Although shown in flat layout view, as should be readily apparent to one skilled in the art in view of this disclosure, tapered stent spring 202 (tapered from one side of the stent graft to a location 180 degrees opposing on the other side) forms an annulus in its final configuration.

Referring to FIGS. 2B and 3 together, tapered stent spring 202 includes a plurality of stent cells 204, including a first stent cell 204A and a second stent cell 204B contiguous with first stent cell 204A. First stent cell 204A is directly coupled to second stent cell 204B to form a part of tapered stent spring 202. In a similar manner, subsequent stent cells 204 are coupled with their respective contiguous stent cells 204 thus forming tapered stent spring 202.

Stent cells 204 are closed, i.e., form a structure with an unbroken perimeter, and are diamond shape. Further, stent cells 204 include upper, e.g., first, apexes 312 and lower, e.g., second, apexes 314 (FIG. 3). Contiguous stent cells 204, such as stent cell 204A and stent cell 204B, are directly coupled at lower apexes 314 and abutting upper apexes 312 of contiguous stent cells 204.

Illustratively, first stent cell 204A includes an upper apex 312A and lower apex 314A. Similarly, contiguous second stent cell 204B includes an upper apex 312B and a lower apex 314B. Lower apex 314A of first tapered stent cell 204A abuts and is directly coupled to upper apex 312B of second tapered stent cell 204B. In a similar manner, subsequent stent cells 204 are coupled at respective abutting apexes 312 and 314 thus forming tapered stent spring 202.

As noted above, stent cells 204 are closed and each forms a diamond shape. With reference to the diamond shape of stent cells 204, stent cells 204 have cell circumferential distances 324 between upper apexes 312 and lower apexes 314 of stent cells 204. As used herein, a circumferential distance is the distance between two points on tapered stent spring 202, e.g., cell circumferential distance 324 between upper apex 312 and lower apex 314, along a circumference which is defined by the annular shape of tapered stent spring 202 and which passes through the two points.

Contiguous stent cells 204, such as stent cell 204A and stent cell 204B, while similarly diamond shaped, vary in size. For example, cell circumferential distance 324A, between upper apex 312A and lower apex 314A, of first stent cell 204A is greater than cell circumferential distance 324B, between upper apex 312B and a lower apex 314B, of second stent cell 204B. The cell circumferential distances 324 of contiguous stent cells 204 of tapered stent springs 202 vary in a similar manner and so are not discussed further.

Also with reference to the diamond shape of stent cells 204, stent cells 204 have left, e.g., third, apexes 315 and right, e.g., fourth, apexes 317 and cell lateral distances 326 therebetween. As used herein, a lateral distance is the distance between two points on tapered stent spring 202, for example left apex 315 and right apex 317, along a lateral axis (not shown) at the circumference of tapered stent spring 202, which is coplanar with and parallel to central axis L of stent graft 200.

Illustratively, first stent cell 204A includes left apex 315A and right apex 317A with a first cell lateral distance 326A therebetween. Second stent cell 204B includes left apex 315B and right apex 317B with second cell lateral distance 326B therebetween.

In a manner similar to the cell circumferential distances 324, first cell lateral distance 326A of first stent cell 204A is greater than second cell lateral distance 326B of contiguous second stent cell 204B. The cell lateral distances 326 of all contiguous stent cells 204 of tapered stent springs 202 vary in a similar manner and so are not discussed further. In addition, as discussed more fully below, tapered stent springs 202 include smallest stent cells 204S, in which cell circumferential distances 324 and cell lateral distances 326, within respective tapered stent springs 202, are minimum.

When viewed in flat layout view as in FIG. 3, tapered stent spring 202 defines an imaginary tapered envelope 316 enclosing tapered stent spring 202. In particular, left apexes 315 of stent cells 204 define a left portion 316L of tapered envelope 316 and right apexes 317 of stent cells 204 define a right portion 316R of tapered envelope 316.

Although stent cells of a diamond shape are described above, in light of this disclosure, it is understood that tapered stent springs may include stent cells of other shapes according to other embodiments. For example, as discussed above in reference to the embodiment of FIG. 2A, integral, wave-like, serpentine shape, tapered stent springs are formed from open stent cells.

Figure 4:
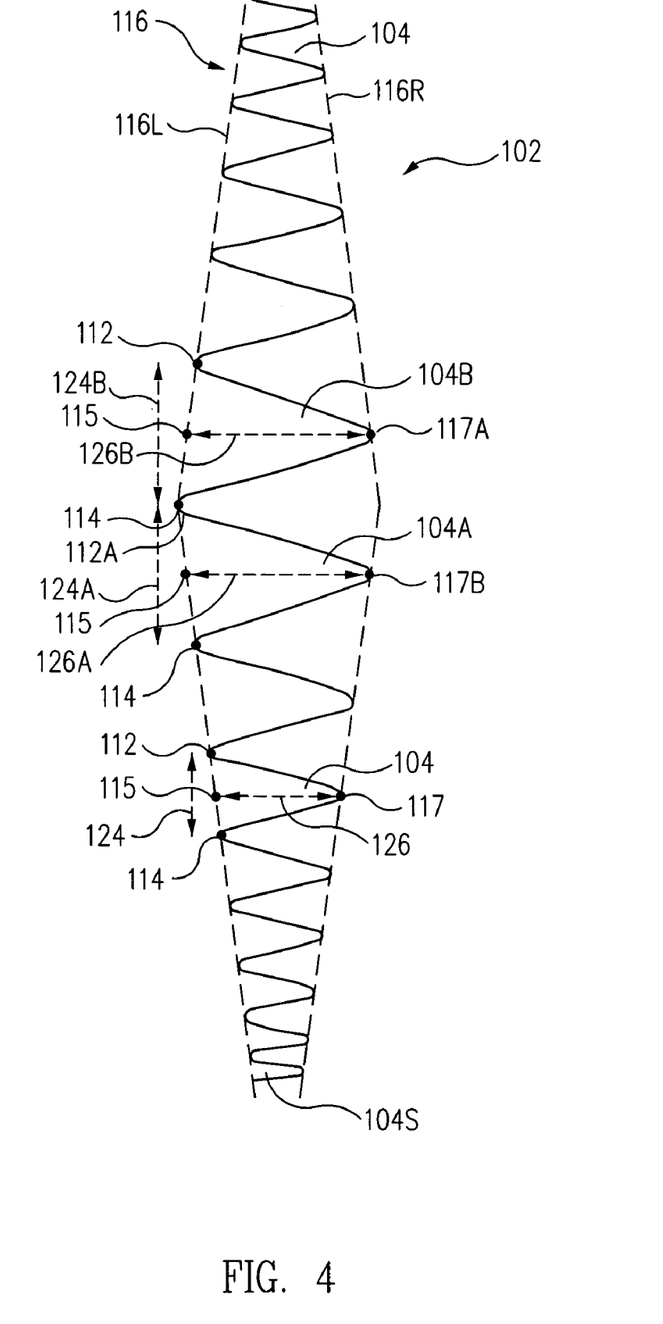
FIG. 4 is a flat layout view of an individual tapered stent spring of the stent graft of FIG. 2A.

More particularly, FIG. 4 is a view an individual tapered stent spring 102 of stent graft 100 of FIG. 2A, depicted in a flat layout view for clarity of presentation. Although shown flat, as should be readily apparent to one skilled in the art in view of this disclosure, tapered stent spring 102 forms an annulus in its final configuration. Tapered stent spring 102 includes a plurality of stent cells 104, including first stent cell 104A and second stent cell 104B contiguous with first stent cell 104A. Further, stent cells 104 include stent cell start, e.g., first, points 112, stent cell end, e.g., second, points 114, stent cell mid—, e.g., third, points 115, and stent cell peak, e.g., fourth, points 117.

As used herein, stent cell start point 112 is a first minima inflection point along serpentine shape stent cell 104. Further, stent cell end point 114 is a second minima inflection point along serpentine shape stent cell 104, subsequent to start point 112. Still further, stent cell mid-point 115 is the point midway between, and co-linear with, stent cell start point 112 and stent cell end point 114. Finally, stent cell peak point 117 is a maxima inflection point along serpentine shape stent cell 104, between stent cell start point 112 and stent cell end point 114.

First stent cell 104A is integrally formed with second stent cell 104B to form a part of tapered stent spring 102. In a similar manner, subsequent stent cells 104 are integrally formed with respective contiguous stent cells 104 thus forming annular shape tapered stent spring 102.

With reference to the serpentine shape of stent cell 104, stent cell 104 has a cell circumferential distance 124 between stent cell start point 112 and stent cell end point 114. Further, stent cell 104 has a stent cell lateral distance 126 between stent cell mid-point point 115 and stent cell peak point 117.

Contiguous stent cells, such as stent cells 104A and 104B while similarly shaped, vary in size. For example, cell circumferential distance 124A of first stent cell 104A is greater than cell circumferential distance 124B of second stent cell 104B. Similarly, cell lateral distance 126A of first stent cell 104A is greater than cell lateral distance 126B of second stent cell 104B. Cell circumferential distances 124 and cell lateral distances 126 of contiguous stent cells 104 of tapered stent spring 102 vary in a similar manner and so are not discussed further. In addition, as discussed more fully below, tapered stent springs 102 include smallest stent cells 104S, in which cell circumferential distances 124 and cell lateral distances 126 are minimum.

When viewed in flat plan view as in FIG. 4, tapered stent spring 102 defines an imaginary tapered envelope 116 enclosing tapered stent spring 102. In particular, stent cell midpoints 115 of stent cells 104 define a left portion 116L of tapered envelope 116 and stent cell peak points 117 of tapered stent springs 102 define a right portion 116R of tapered envelope 116.

Figure 5A:
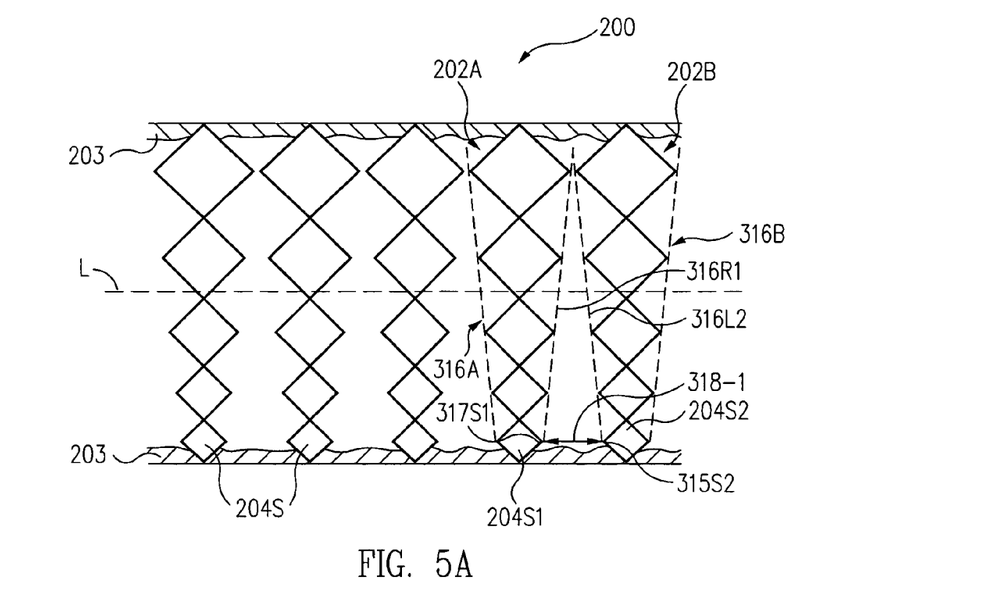
FIG. 5A is an enlarged view of the region V of FIG. 2B of stent graft 200 before deployment.
Figure 5B:
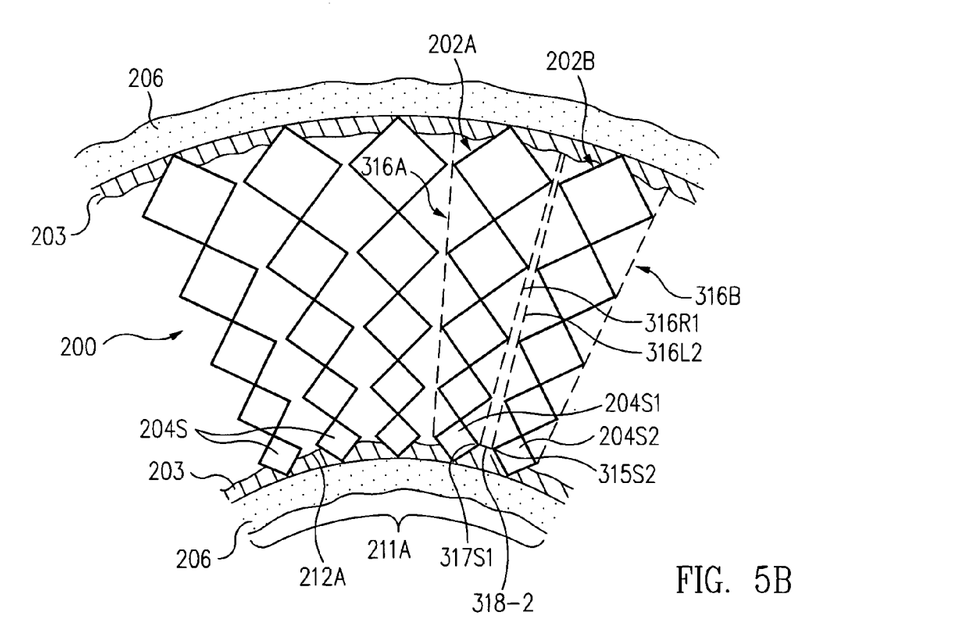
FIG. 5B is an enlarged view of the region V of FIG. 2C of the stent graft deployed in a first curved segment of the artery system.

Referring now to FIGS. 5A and 5B, FIG. 5A is an enlarged view of the region V of FIG. 2B of stent graft 200 before deployment and FIG. 5B is an enlarged view of the region V of FIG. 2C with stent graft 200 deployed in first curved segment 211A of artery system 206. Stent graft 200 includes first tapered stent spring 202A and adjacent second tapered stent spring 202B spaced apart on cylindrical stent graft material 203.

First tapered stent spring 202A includes a smallest stent cell 204S1 of first tapered stent spring 202A. Further, first tapered stent spring 202A defines a first imaginary tapered envelope 316A. Second tapered stent spring 202B includes a smallest stent cell 204S2 of second tapered stent spring 202B. Further, second tapered stent spring 202B defines a second imaginary tapered envelope 316B.

Referring to FIGS. 2B, 5A and 5B together, as noted above, stent graft 200 is well suited for deployment in artery system 206. As discussed more fully below, prior to expansion stent graft 200 is rotationally, i.e., angularly about central axis L of stent graft 200, positioned within artery system 206 such that smallest stent cells 204S, such as smallest stent cell 204S1 of first tapered stent spring 202A and smallest stent cell 204S2 of second tapered stent spring 202B, are placed along a first curved segment inside radius 212A of first curved segment 211A of artery system 206. In one embodiment, radio opaque markers (not shown), well know to those of ordinary skill in the art, are used to rotationally orient stent graft 200 within artery system 206.

Use of stent graft 200 that includes rotational positioning of smallest stent cells 204S of tapered stent springs 202 along first curved segment inside radius 212A of first curved segment 211A of artery system 206 allows deployed stent graft 200 to easily conform to first curved segment 211A of artery system 206 while maintaining support for artery system 206. Such rotational positioning of smallest stent cells 204S within artery system 206 avoids restriction of blood flow through artery system 206 resulting from binding or kinking of the stent graft at first curved segment 211A.

As shown in the FIGS. 5A and 5B, the spacing between adjacent stent springs 202 changes after stent graft 200 is deployed at first curved segment 211A of artery system 206. Specifically, the spacing between a right portion 316R1 of imaginary tapered envelope 316A of first tapered stent spring 202A and a left portion 316L2 of imaginary tapered envelope 316B of second tapered stent spring 202B changes at first curved segment 206 before (FIG. 5A) and after (FIG. 5B) deployment of stent graft 200.

More particularly, the spacing between corresponding smallest stent cells 204S1 and 204S2 on adjacent tapered stent springs 202A and 202B, respectively, is different before and after deployment at first curved segment 211A of artery system 206. As used herein, stent cells 204 on adjacent tapered stent springs 202 are said to be corresponding when stent cells 204 occupy the same relative positions, respectively, on adjacent tapered stent springs 202.

By way of illustration, before deployment (FIG. 5A), at the portion of stent graft 200 intended for deployment at first curved segment 211A of artery system 206, smallest stent cell 204S1 of first tapered stent spring 202A and corresponding smallest stent cell 204S2 of second tapered stent spring 202B are spaced apart by a first spacing distance 318-1 between right apex 317S1 of smallest stent cell 204S1 of first tapered stent spring 202A and left apex 315S2 of corresponding smallest stent cell 204S2 of second tapered stent spring 202B.

Further, after deployment (FIG. 5B), at first curved segment 211A of artery system 206, smallest stent cell 204S1 of first tapered stent spring 202A and corresponding smallest stent cell 204S2 of second tapered stent spring 202B are spaced apart by a second spacing distance 318-2 between right apex 317S1 of smallest stent cell 204A of first tapered stent spring 202A and left apex 315S2 of corresponding smallest stent cell 204S2 of second tapered stent spring 202B.

Corresponding smallest stent cells 204S1 and 204S2 on adjacent stent springs 202A and 202B, respectively, are spaced apart a relatively large first spacing distance 318-1 prior to deployment at first curved segment 211A. Thus stent graft 200 may axially bend, to conform with first curved segment 211A, without overlap of corresponding smallest stent cells 204S1 and 204S2 positioned at first curved segment inside radius 212A.

After deployment at first curved segment 211A, corresponding smallest stent cells 204S1 and 204S2 are pinched more closely together by the bending force imposed by first curved segment 211A. Thus, first spacing distance 318-1 (FIG. 5A) is greater than second spacing distance 318-2 (FIG. 5B), allowing stent graft 200 to conform to the curved shape of artery system 206 at first curved segment 211A.

In another embodiment according to the present invention, stent graft 200 may include multiple pluralities of tapered stent springs 202. Referring again to FIG. 2B and 2C, the portion of stent graft 200 deployed at first curved segment 211A of artery system 206 includes a first plurality of tapered stent springs 209A (FIG. 2B) that provides axial flexibility to stent graft 200 in one direction. Similarly, the portion of stent graft 200 deployed at a second curved segment 211B (FIG. 2C) of artery system 206 includes a second plurality of tapered stent springs 209B (FIG. 2B) that provides axial flexibility to stent graft 200 in another direction.

Rotational positioning of smallest stent cells 204S of stent springs 202 at first curved segment inside radius 212A provides axial flexibility to stent graft 200 in one direction. Rotational positioning of smallest stent cells 204S of stent springs 202 at second curved segment inside radius 212B provides axial flexibility to stent graft 200 in a second direction.

Since, axial flexibility may be provided to stent graft 200 in more than one direction, stent graft 200 may be made to conform to body lumens containing compound curves. Thus, stent grafts for special applications, such as thoracic stent grafts at the arch level, abdominal stent grafts in the case of an angulated segment just distal to proximal neck fixation, or abdominal stent grafts at the iliac legs, are formed with embodiments of stent springs as discussed above.

Although stent springs forming a single stent graft is described above, in light of this disclosure, it is understood that stent springs formed according to the present invention may be utilized in forming a bifurcated stent graft that includes a first stent graft and a second stent graft for use in conjunction with the first stent graft.

This disclosure provides exemplary embodiments of the present invention. The scope of the present invention is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A stent graft comprising:
    a cylindrical shape stent graft material; and
    tapered stent springs coupled to said stent graft material, wherein each of said tapered stent springs comprising stent cells, said stent cells tapering to a smallest stent cell; and
    wherein said smallest stent cells of said tapered stent springs are rotationally positioned on said stent graft material at the same relative position.

2. The stent graft of claim 1 wherein said stent graft material is inside said tapered stent springs.

3. The stent graft of claim 1 wherein said stent graft material is outside said tapered stent springs.

4. The stent graft of claim 1 wherein said tapered stent springs comprise a first tapered stent spring comprising:
    a first stent cell; and
    a second stent cell contiguous with said first stent cell.

5. The stent graft of claim 4 wherein said second stent cell is coupled to said first stent cell.

6. The stent graft of claim 5 wherein said second stent cell is smaller than said first stent cell.

7. The stent graft of claim 5 wherein said first stent cell and said second stent cell are closed.

8. The stent graft of claim 5 wherein said first stent cell and said second stent cell are diamond shape.

9. The stent graft of claim 4 wherein said first stent cell and said second stent cell are integral.

10. The stent graft of claim 9 wherein said first stent cell and said second stent cell are open.

11. The stent graft of claim 9 wherein said first stent cell and said second stent cell are serpentine shape.

12. The stent graft of claim 9 wherein said serpentine shape is selected from the group consisting of zigzag, and stepped.

13. A stent graft comprising:
    a cylindrical shape stent graft material;
    a first tapered stent spring coupled to said stent graft material, said first tapered stent spring comprising stent cells, said stent cells tapering to a smallest stent cell of said first tapered stent spring; and
    a second tapered stent spring coupled to said stent graft material and adjacent to said first tapered stent spring, said second tapered stent spring comprising stent cells, said stent cells of said second tapered stent spring tapering to a smallest stent cell of said second tapered stent spring, wherein said smallest stent cell of said first tapered stent spring and said smallest stent cell of said second tapered stent spring are rotationally positioned on said stent graft material at the same relative position, wherein said second tapered stent spring is spaced apart from said first tapered stent spring by a spacing distance.

14. The stent graft of claim 13 wherein said first tapered stent spring and said second tapered stent spring are coupled to said stent graft material by sutures.

15. The stent graft of claim 13 wherein said spacing distance decreases as said stent graft is bent.

16. A stent graft comprising:
    tapered stent spring means comprising:
        stent cell means tapering to smallest stent cells;
    cylindrical shape support means for supporting said tapered stent spring means; and
    means for coupling said tapered stent spring means to said cylindrical shape support means, wherein said smallest stent cells of said stent cell means are rotationally positioned on said cylindrical shape support means at the same relative position.

* * * * *

UNITED STATES PATENT AND TRADEMARK OFFICE
CERTIFICATE OF CORRECTION

PATENT NO. : 7,279,003 B2
APPLICATION NO. : 10/423163
DATED : October 9, 2007
INVENTOR(S) : Humberto Berra et al.

It is certified that error appears in the above-identified patent and that said Letters Patent is hereby corrected as shown below:

Column 7, line 38, "stent cells, said stent cells tapenng to a smallest stent" should be changed to -- stent cells, said stent cells tapering to a smallest stent --

Signed and Sealed this

Eleventh Day of November, 2008

JON W. DUDAS
*Director of the United States Patent and Trademark Office*